United States Patent
Pavelka

(10) Patent No.: US 9,355,870 B1
(45) Date of Patent: May 31, 2016

(54) INTEGRATED CIRCUIT WITH SENSOR AREA AND RESIN DAM

(71) Applicant: Silicon Laboratories Inc., Austin, TX (US)

(72) Inventor: John B. Pavelka, Austin, TX (US)

(73) Assignee: Silicon Laboratories Inc., Austin, TX (US)

( * ) Notice: Subject to any disclaimer, the term of this patent is extended or adjusted under 35 U.S.C. 154(b) by 0 days.

(21) Appl. No.: 14/597,293

(22) Filed: Jan. 15, 2015

(51) Int. Cl.
| | |
|---|---|
| H01L 21/56 | (2006.01) |
| H01L 23/31 | (2006.01) |
| G01N 27/12 | (2006.01) |
| G01N 25/00 | (2006.01) |
| G01N 33/00 | (2006.01) |
| G01F 1/00 | (2006.01) |

(52) U.S. Cl.
CPC ............... *H01L 21/565* (2013.01); *G01F 1/00* (2013.01); *G01N 25/00* (2013.01); *G01N 27/121* (2013.01); *G01N 33/0036* (2013.01); *H01L 23/3107* (2013.01)

(58) Field of Classification Search
CPC ............ H01L 21/4825; H01L 21/28079; H01L 23/53235; H01L 23/53219; H01L 23/53242; H01L 23/4951; H01L 27/0922; H01L 27/0814; H01L 29/6603; H01L 51/5296; H01L 51/0034; H01L 41/1132
USPC ............ 438/75, 124, 141, 328, 686, 687; 257/292, 484, E21.006, E21.007, 257/E21.053, E21.126, E21.127, E21.352, 257/E21.366, E21.499, E21.503, E21.509
See application file for complete search history.

(56) References Cited

U.S. PATENT DOCUMENTS

| | | | |
|---|---|---|---|
| 6,191,359 B1* | 2/2001 | Sengupta | ............... H01L 23/10 174/538 |
| 6,686,227 B2* | 2/2004 | Zhou | ............... H01L 21/565 438/127 |
| 6,815,262 B2 | 11/2004 | Hundt et al. | |
| 6,858,933 B2 | 2/2005 | Abela et al. | |
| 7,202,110 B2 | 4/2007 | Chiu et al. | |
| 7,244,967 B2* | 7/2007 | Hundt | ............... H01L 21/565 257/99 |
| 7,901,971 B2 | 3/2011 | Hunziker et al. | |
| 8,890,308 B2 | 11/2014 | Hooper et al. | |
| 2013/0264692 A1 | 10/2013 | Hooper et al. | |
| 2014/0206122 A1 | 7/2014 | Fernandez et al. | |

FOREIGN PATENT DOCUMENTS

WO    WO2006/114005 A1    4/2005

* cited by examiner

*Primary Examiner* — David Nhu
(74) *Attorney, Agent, or Firm* — Egan, Peterman, Enders & Huston LLP

(57) ABSTRACT

A technique for forming an integrated circuit die that contains an integrated sensor is provided. The integrated circuit die may be configured such that the sensor is exposed to ambient environmental conditions such that the sensor may detect ambient conditions. The integrated circuit die may be generally protected from environmental exposure by a mold resin. The mold resin may be formed in areas outside of a sensor region. Resin bleed from the mold resin into the sensor region may be prevented by the use of a resin dam that extends from the surface of the integrated circuit die. The resin dam may surround the sensor region.

23 Claims, 5 Drawing Sheets

VIEW A

US 9,355,870 B1

INTEGRATED CIRCUIT WITH SENSOR AREA AND RESIN DAM

FIELD OF THE INVENTION

The present disclosure relates to the field of integrated circuits. More specifically, it relates to integrated circuits which include the integration of sensor structure.

BACKGROUND

The current generation of sensor devices is migrating to an integration of the sensor structure directly onto an integrated circuit die, which serves to condition and process the signals generated by the sensor. Some of these sensors, such as humidity, gas detection, and flow rate sensors, must be exposed directly to the ambient environment to take their readings. In general, the ambient environment measured by these sensors is not compatible with the materials of the integrated circuit die and may cause reliability problems if the die is exposed to this environment for an extended period.

A solution to this problem, in practice now, is to transfer mold the integrated circuit device with an epoxy resin, as is typically done for plastic-molded electronic packages. However, during the molding process, a sensor port is built into the package such that the sensor area of the die is exposed to ambient conditions, but the remainder of the die is safely encapsulated in the mold resin. A common method to form this sensor port is to use a technique known as Film-Assisted Molding (FAM).

Film-Assisted Molding incorporates a compressible film between the molding insert and the surface of the integrated die (sensor area). The film accommodates variations in the die thickness and surface topology to create a seal, preventing mold resin from bleeding into the area that must be kept clear for the sensor. Unfortunately, this film has a relatively small range of accommodation—too little compression of the film and resin will bleed under the film. Too much compression of the film, and there is a high risk that the sensor or die will incur mechanical damage, such as die cracking, embossing of the sensor surface, etc.

The current disclosure describes a method to significantly increase the range of film accommodation, thereby preventing resin bleed onto the sensor area, while eliminating mechanical damage to the sensor or die.

SUMMARY

The disclosure herein describes a technique for forming substrate that contains a sensor. In one embodiment the substrate may be an integrated circuit die, however, the concepts described herein are applicable to other more general uses of substrates that have sensors. The integrated circuit die may be configured such that the sensor is exposed to ambient environmental conditions such that the sensor may detect ambient conditions. The integrated circuit die may be generally protected from environmental exposure by a mold resin. The mold resin may be formed in areas outside of a sensor region. Resin bleed from the mold resin into the sensor region may be prevented by the use of a resin dam that extends from the surface of the integrated circuit die. The resin dam may surround the sensor region.

In one embodiment, an sensor device is provided. The sensor device may comprise substrate and a sensor region of said substrate, said sensor region configured to allow for an ambient access region of an ambient sensor of said substrate. The substrate may further include a first resin dam on said substrate, the first resin dam extending above a surface of the substrate. The substrate may further comprise a mold resin on the substrate, the first resin dam being located between the sensor region and the mold resin. In one embodiment the substrate may be an integrated circuit die.

In another embodiment, an integrated ambient sensor is provided. The integrated ambient sensor may comprise an integrated circuit die and a sensor region formed in an upper region of the integrated circuit die, the sensor region configured to allow for an ambient environmental condition to be exposed to the sensor region. The integrated ambient sensor may further include a mold resin surrounding the sensor region, the mold resin configured to protect the integrated circuit from ambient conditions other than in said sensor region. The integrated ambient sensor may further include a resin dam surrounding the sensor region, the resin dam providing a barrier between the mold resin and the sensor region.

In yet another embodiment, a method of packaging an integrated circuit having an ambient sensor is provided. The method may include providing an integrated circuit die, the integrated circuit die having a ambient sensor region located in an upper region of the integrated circuit die. The method may further comprise providing at least one resin dam on a surface of the integrated circuit die, the at least one resin dam surrounding the ambient sensor region. The method may further comprise utilizing a mold insert and a mold film to form a high compression zone between the mold film and the resin dam. The method may further comprise utilizing the resin dam and high compression zone to block resin bleed from entering the ambient sensor region during formation of the mold resin on said integrated circuit.

BRIEF DESCRIPTION OF THE DRAWINGS

A more complete understanding of the present disclosure and advantages thereof may be acquired by referring to the following description taken in conjunction with the accompanying drawings, in which like reference numbers indicate like features. It is to be noted, however, that the accompanying drawings illustrate only exemplary embodiments and are therefore not to be considered limiting of its scope, for the invention may admit to other equally effective embodiments.

DETAILED DESCRIPTION

A more complete understanding of the present invention and advantages thereof may be acquired by referring to the following description taken in conjunction with the accompanying drawings, in which like reference numbers indicate like features. It is to be noted, however, that the accompanying drawings illustrate only exemplary embodiments of the disclosed concept and are therefore not to be considered limiting of its scope, for the disclosed concept may admit to other equally effective embodiments.

Figure 1:
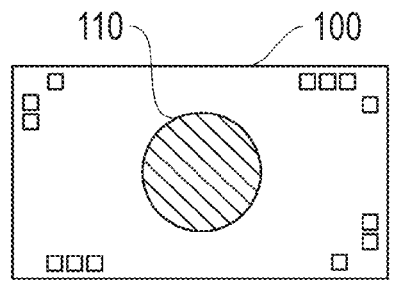
FIG. 1—(Prior Art)—Top view representation of an integrated circuit having an integrated sensor area.
Figure 1A:
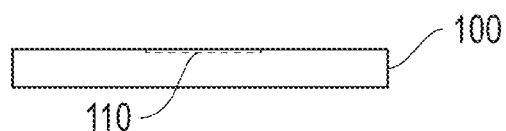
FIG. 1A—(Prior Art)—Cross-section of the integrated circuit of FIG. 1.

An integrated circuit die 100 with integrated sensor area 110 is shown in FIG. 1. As the techniques described herein are not limited to any particular type of integrated circuit, this could be any typical integrated circuit die, such as CMOS, SiGe, GaAs, etc, integrated circuits. A sensor structure is integrated on the die in the sensor area 110. By being integrated, the sensor structure may communicate directly with the circuitry of the integrated circuit die. The sensor may be used to detect one or more aspects of the ambient environment, such as humidity, gas composition, flow rate, temperature, biological detection, etc. As the techniques described here are not limited to any particular type of sensor, it will be recognized that the techniques described herein may be utilized with a wide range of ambient sensors. In general, the sensor area will be exposed to the ambient environment, while the remainder of the integrated circuit die is encapsulated in mold resin to assure long-term reliability of the die.

Figure 2:
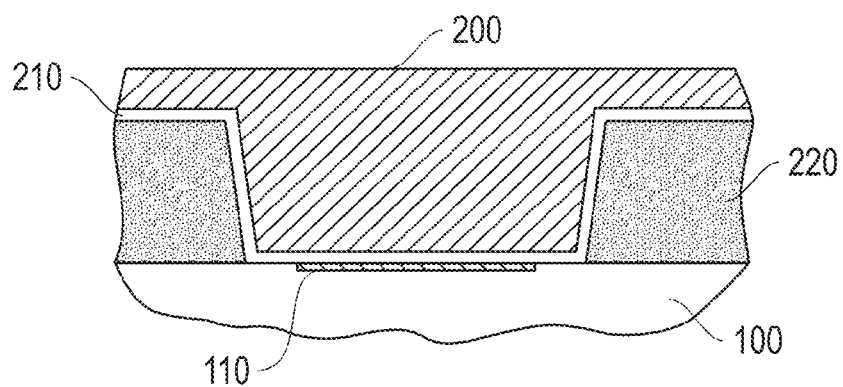
FIG. 2—(Prior Art)—Expanded cross-section of the integrated circuit of FIG. 1A.
Figure 3:
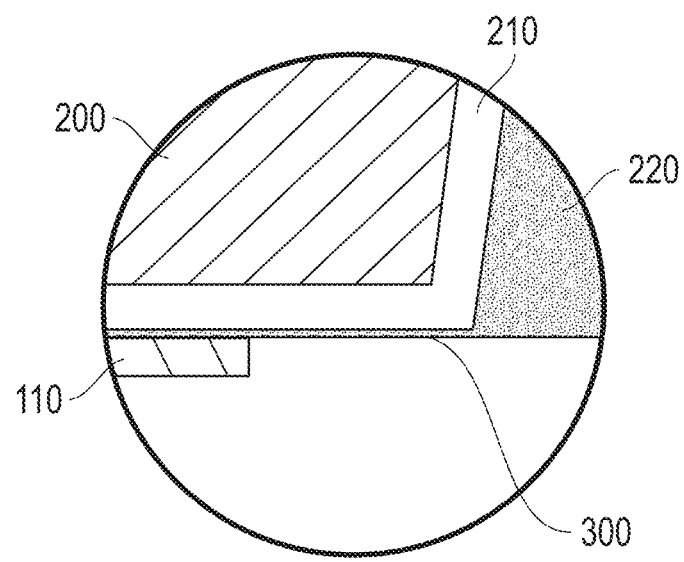
FIG. 3—(Prior Art)—Further expanded cross-section of the integrated circuit of FIG. 1A.

Film-Assisted Molding (FAM) is a commonly used method to mold a sensor port into the device package, thereby exposing the sensor area while encapsulating the remainder of the die. A schematic of the FAM set-up is shown in FIG. 2. The integrated circuit die 100, with sensor area 110, is shown in cross section. A piston, or other shaped, mold insert 200 in the mold tool defines the sensor port area that will be free of mold resin 220 after molding. A compliant film 210 is placed between the mold insert 200 and integrated circuit die 100. This film 210 provides mechanical compliance between the integrated circuit die 100 and the mold insert 200. Variations such as die thickness and surface topology are accommodated through compression of the film to conform to the integrated circuit surface. In addition, a sufficient level of film compression must be achieved to off-set the pressure of the liquid mold resin as it is injected into the mold cavity. If the film is not compressed sufficiently, the resin will bleed under the film, contaminating the sensor area (FIG. 3). If too much pressure is applied to the mold film the force transmitted to the integrated circuit die may result in mechanical damage, such as die cracking, surface damage, or deformation/embossing of the sensor itself. Unfortunately, the range of accommodation for the mold film is very limited, resulting in a very tight process window, which is difficult to control in high-volume production.

FIG. 3 shows an expanded view of the integrated circuit die 100 cross section of FIG. 2. FIG. 3 illustrates an example of resin bleed. As shown in FIG. 3, when the mold film 210 is not sufficiently compressed undesirable resin bleed 300 may result in an area between the mold film 210 and the top of the integrated circuit die 100.

A solution to the resin bleed problem is to add a resin dam structure to the integrated circuit die, as shown in FIGS. 4, 5, 6 and 7. As shown in the figures, a dam 400 is formed on the integrated circuit die. The dam 400 may be formed in a wide variety of manners and take any of a variety of shapes. Though called a "dam" it will be recognized that the dam may take the form of, for example but not limited to, bumps, protrusions, projections, extensions, humps, ridges, bulges, etc. extending above the surrounding areas of the integrated circuit. It will be recognized that "dam" as used herein would encompass all such structures and any other structures that may act to block the flow of resin.

Figure 4:
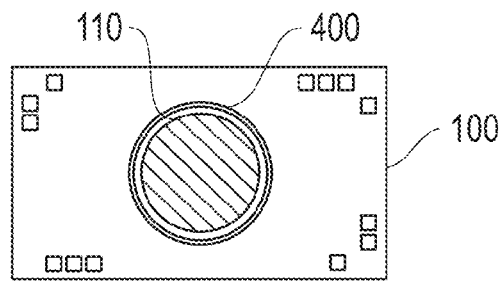
FIG. 4—Top view representation of an integrated circuit having an integrated sensor area and a resin dam.

In one embodiment as shown in FIG. 4, the resin dam 400 may be formed in a ring shape around the sensor area 110. It will be recognized that the dam may form other shapes and still achieve its purposes. Thus, other shapes such as oblongs, squares, rectangles, etc. may be used. Further, though shown as an enclosed shape, it will be recognized that the advantages of the use of a resin dam as described herein may be achieved by the use of resin dam that may have some limited unenclosed regions.

Figure 7:
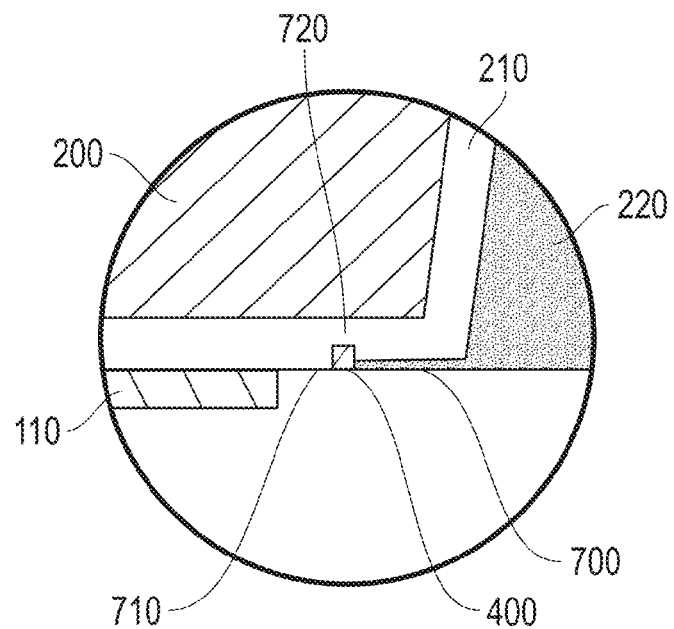
FIG. 7—Further expanded cross-section of view A of the integrated circuit of FIG. 5 showing resin bleed blocked by the resin dam.

As shown in top view FIG. 4, the dam structure 400 is formed around the sensor area 110. The dam structure 400 serves as a physical dam, preventing mold resin 220 from traveling laterally into the sensor area 110 of the integrated circuit die. The dam structure 400 also pre-compresses the mold film 210 when the mold insert 200 is utilized, resulting in a localized high-compression zone 720 in the film around the dam. The high-compression zone 720 in the mold film 210 forms a tight seal between the mold film 210 and the dam 400, without transmitting excessive force to the integrated circuit die surface (FIG. 7). With the resin dam 400 blocking resin bleed, the mold compression force can be reduced, thereby eliminating mechanical damage to the die and improving manufacturing yields.

Figure 4A:
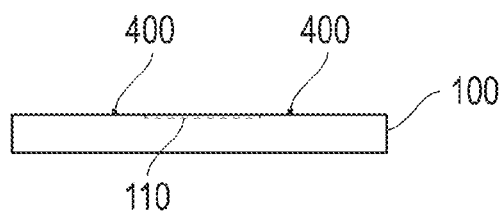
FIG. 4A—Cross-section of the integrated circuit of FIG. 4.
Figure 4B:
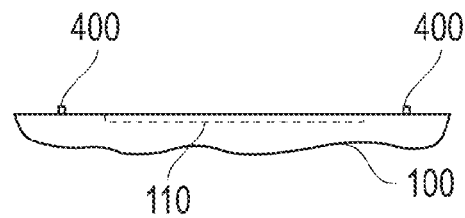
FIG. 4B—Expanded cross-section of the integrated circuit of FIG. 4.
Figure 5:
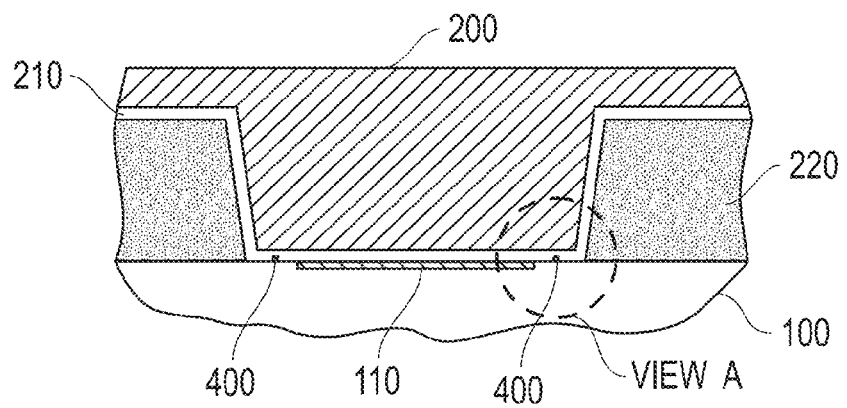
FIG. 5—Further expanded cross-section of the integrated circuit of FIG. 4.
Figure 6:
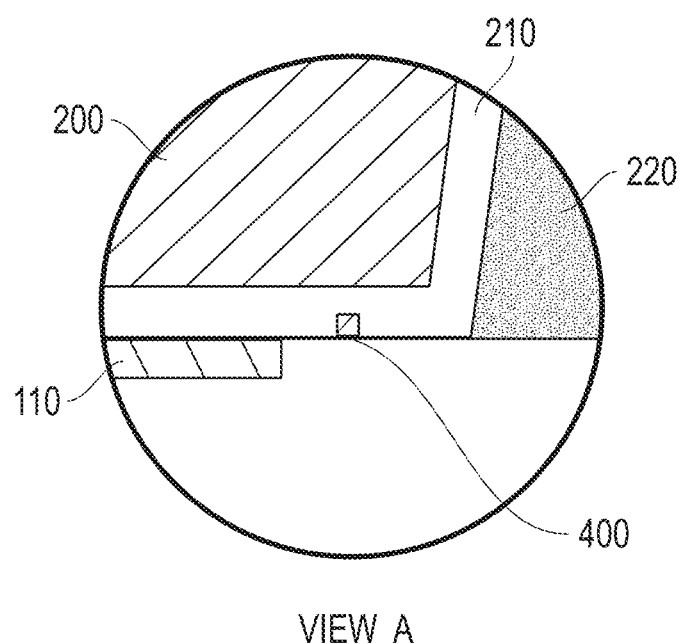
FIG. 6—Further expanded cross-section of view A of the integrated circuit of FIG. 5.

A cross section of the integrated circuit die utilizing a dam 400 around the sensor area 110 is shown in FIG. 4A and more expanded in FIG. 4B. FIG. 5 illustrates the integrated circuit die 100 utilizing a dam 400 around the sensor area 110 and the use of the mold insert 200, mold film 210, and mold resin 220. FIG. 6 illustrates an expanded cross section of View A of FIG. 5. As shown in FIGS. 5 and 6 resin bleed is not present. However, FIG. 7 illustrates the expanded cross section View A of FIG. 5 and the presence of resin bleed. As shown in FIG. 7, the resin bleed is blocked by the dam 400 at the high compression zone 720 of the mold film 210. In this manner, resin bleed may be blocked from the sensor area 110, preventing resin contamination of the sensor area 110.

The resin dam can be fabricated from a variety of materials such as metals (copper, aluminum, gold, etc.) or polymers (polyimide, PBO, epoxy, etc.). It will be recognized, however, that a wide range of other materials will also provide the function of the dam 400 so that the concepts described herein are not limited to these materials. The mold film may be any of a wide variety of materials including any of a wide variety of polymers. In one embodiment, it is desirable that the modulus of the dam material be sufficient to create a pre-compression zone in the mold film.

Standard process methods can be employed to fabricate the dam. In one exemplary embodiment a metal-ring, formed by plating-up metal may be utilized. In such an embodiment the metal is plated-up on the integrated circuit wafer and then the ring structure is defined through photolithography as is typically done for flip-chip, copper-pillar, or gold-bumping processes. An exemplary dam material may be gold, as gold is resistant to corrosion and will generally not degrade if exposed to harsh physical or chemical conditions in the sensing environment. In one exemplary embodiment a ring shaped dam having a dam width of approximately 20 um and dam height of approximately 20 um (1:1 aspect ratio) is utilized to minimize resin bleed. However, as will be recognized, other dam materials, dam designs and dam sizes may be used to tailor the dam to different applications.

Figure 8:
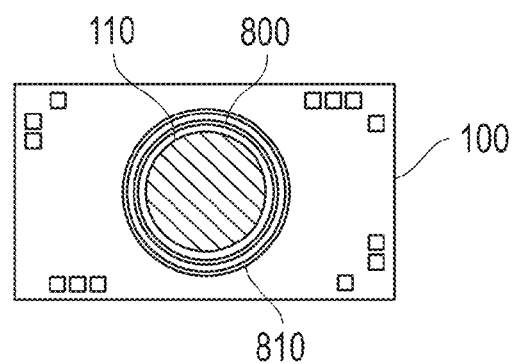
FIG. 8—Top view representation of an integrated circuit having an integrated sensor area, an inner ring resin dam and an outer ring resin dam.

One exemplary alternate embodiment of the dam is shown in FIG. 8. As shown in FIG. 8, a dual dam structure is utilized. Thus, an first dam 800 (the inner dam) and a second dam 810 (the outer dam) are provided. The double dam structure creates a "moat" between the first dam 800 and second dam 810. Any resin that manages to bleed past the outer dam (dam 810)

will drop into this gap prior to approaching the inner dam (dam 800). Bleed past the inner dam will be quite difficult as there will be a significant drop in resin pressure after passing the outer dam. Unless there is a significant breach of the outer dam, the moat will provide a sufficient reservoir to hold the resin bleed until resin cure is completed. As will be recognized, more than one dam may also be utilized and a wide variety of shapes and sizes of a plurality of dams utilized to assist the blockage of resin bleed may be utilized, all of which may be mere design choice for one skilled in the art depending upon a particular application.

Thus, as described herein a molding process is provided in that a mold insert and mold film may be utilized in conjunction with a resin dam during an integrated circuit package molding manufacturing process. The resultant integrated circuit structure will have a mold resin that encapsulates the integrated circuit to protect the integrated circuit die, except the encapsulation does not cover the sensor area. Resin bleed may exist in a region adjacent one side of the resin dam, however, such resin bleed will not extend past the resin dam into the sensor area.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as presently preferred embodiments. Equivalent elements may be substituted for those illustrated and describe herein and certain features of the invention may be utilized independently of the use of other features, all as would be apparent to one skilled in the art after having the benefit of this description of the invention.

What is claimed is:

1. An sensor structure comprising:
   a substrate;
      a sensor region of said substrate, said sensor region configured to allow for an ambient access region of an ambient sensor of said substrate
      a first resin dam on said substrate, the first resin dam extending above a surface of the substrate and
      a mold resin on the substrate, the first resin dam being located between the sensor region and the mold resin, wherein the first resin dam provides a barrier between the mold resin and the sensor region.

2. The sensor structure of claim 1, wherein the first resin dam completely surrounds the sensor region.

3. The sensor structure of claim 2, wherein the first resin dam is ring shaped.

4. The sensor structure of claim 1, wherein the substrate is an integrated circuit die.

5. The sensor structure of claim 4, wherein the first resin dam completely surrounds the sensor region.

6. The sensor structure of claim 4, wherein the first resin dam is ring shaped.

7. The sensor structure of claim 4, wherein the first resin dam has a height to width aspect ratio of approximately 1:1.

8. The sensor structure of claim 4, wherein the first resin dam comprises gold.

9. The sensor structure of claim 4, further comprising a second resin dam, a moat region being formed between the first resin dam and the second resin dam.

10. The sensor structure of claim 4, the sensor being at least one of a humidity sensor, a gas composition sensor, a flow rate sensor, a temperature sensor, or a biological detection sensor.

11. The sensor structure of claim 4, further comprising a resin bleed portion of the mold resin, the resin bleed portion terminating at the resin dam.

12. An integrated ambient sensor, comprising:
   an integrated circuit die
   a sensor region formed in an upper region of the integrated circuit die, the sensor region configured to allow for an ambient environmental condition to be exposed to the sensor region;
   a mold resin surrounding the sensor region, the mold resin configured to protect the integrated circuit from ambient conditions other than in said sensor region; and
   a resin dam surrounding the sensor region, the resin dam providing a barrier between the mold resin and the sensor region.

13. The integrated circuit of claim 12, wherein the resin dam is ring shaped.

14. The integrated circuit of claim 12, wherein the resin dam has a height to width aspect ratio of approximately 1:1.

15. The integrated circuit of claim 12, wherein the resin dam is a first resin dam, the integrated circuit further comprising a second resin dam surrounding the first resin dam, a moat region being formed between the first resin dam and the second resin dam.

16. The integrated circuit of claim 12, the sensor being at least one of a humidity sensor, a gas composition sensor, a flow rate sensor, a temperature sensor, or a biological detection sensor.

17. The integrated circuit of claim 12, further comprising a resin bleed portion of the mold resin, the resin bleed portion terminating at the resin dam.

18. A method of packaging an integrated circuit having an ambient sensor, comprising:
   providing an integrated circuit die, the integrated circuit die having a ambient sensor region located in an upper region of the integrated circuit die;
   providing at least one resin dam on a surface of the integrated circuit die, the at least one resin dam surrounding the ambient sensor region;
   utilizing a mold insert and a mold film to form a high compression zone between the mold film and the resin dam; and
   utilizing the resin dam and high compression zone to block resin bleed from entering the ambient sensor region during formation of a mold resin on said integrated circuit.

19. The method of claim 18, wherein the at least one resin dam is ring shaped.

20. The method of claim 18, wherein the at least one resin dam has a height to width aspect ratio of approximately 1:1.

21. The method of claim 18, wherein the at least one resin dam comprises at least one gold resin dam.

22. The method of claim 18, when the at least one resin dam comprises at least two resin dams.

23. The method of claim 18, further comprising providing a mold resin configured to encapsulate the integrated circuit except in the ambient sensor region, the mold resin including a resin bleed portion, the resin bleed portion terminating at the resin dam.

* * * * *